United States Patent
Desel et al.

(10) Patent No.: US 8,906,389 B2
(45) Date of Patent: Dec. 9, 2014

(54) DETERMINATION OF THE EFFICACY OF AN ANTI-MYCOBACTERIAL VACCINATION

(75) Inventors: Christiane Desel, Nuremberg (DE); Stefan H. E. Kaufmann, Berlin (DE); Silke Bandermann, Berlin (DE); Leander Grode, Braunschweig (DE)

(73) Assignees: Max-Planck-Gesellschaft zur Foerderung der Wissenschaften e.V., Munich (DE); Vakzine Projekt Management GmbH, Hannover (DE)

( * ) Notice: Subject to any disclaimer, the term of this patent is extended or adjusted under 35 U.S.C. 154(b) by 0 days.

(21) Appl. No.: 13/996,832

(22) PCT Filed: Dec. 21, 2011

(86) PCT No.: PCT/EP2011/073609
§ 371 (c)(1),
(2), (4) Date: Jun. 21, 2013

(87) PCT Pub. No.: WO2012/085099
PCT Pub. Date: Jun. 28, 2012

(65) Prior Publication Data
US 2013/0280739 A1    Oct. 24, 2013

Related U.S. Application Data

(60) Provisional application No. 61/425,442, filed on Dec. 21, 2010.

(51) Int. Cl.
*A61K 39/04* (2006.01)
*A61K 49/00* (2006.01)
*G01N 33/53* (2006.01)
*G01N 33/68* (2006.01)
*G01N 33/50* (2006.01)

(52) U.S. Cl.
CPC .......... *G01N 33/6869* (2013.01); *A61K 39/04* (2013.01); *G01N 33/505* (2013.01); *G01N 33/5091* (2013.01); *G01N 2333/35* (2013.01); *G01N 2800/52* (2013.01)

USPC ....... 424/248.1; 424/9.1; 424/9.2; 424/234.1; 435/4; 435/6.15; 435/7.1

(58) Field of Classification Search
USPC ................. 424/234.1, 248.1; 435/4, 6.15, 7.1
See application file for complete search history.

(56) References Cited

FOREIGN PATENT DOCUMENTS

| CN | 1798762 A | 7/2006 |
|---|---|---|
| WO | 2004094469 A1 | 11/2004 |
| WO | 2010046039 A1 | 4/2010 |

OTHER PUBLICATIONS

Kauffman, S.H.E., et al. Microbes and Infection, vol. 11, No. 5, pp. 579-583, 2009.*
S.C. De Cassan et al: "Investigating the Induction of Vaccine-Induced Th17 and Regulatory T Cells in Healthy, Mycobacterium bovis BCG-Immunized Adults Vaccinated with a New Tuberculosis Vaccine, MVA85A", Clinical and Vaccine Immunology, vol. 17, No. 7, May 19, 2010, pp. 1066-1073, XP55020193, Stanford CA USA ISSN: 1556-6811, DOI: 10.1128/CVI.00047-10 Abstract.
C. Desel et al: "Recombinant BCG ureC hly+ Induces Superior Protection Over Parental BCG by Stimulating a Balanced Combination of Type 1 and Type 17 Cytokane Responses", The Journal of Infectious Diseases, vol. 204, No. 10, Sep. 20, 2011, pp. 1573-1584, XP55020207, Chicago IL USA ISSN: 0022-1899, DOI: 10.1093/infdis/jir592 the whole document.
Jay K Kolls: "Th17 cells in mucosal immunity and tissue inflammation", Seminars in Immunopathology, vol. 32, No. 1, Feb. 25, 2010, pp. 1-2, XP019800830, Springer, Berlin, ISSN: 1863-2300, p. 1, col. 1, abstract, lines 7-10.
Yinyao Lin et al: "Th17 cytokines and vaccine-induced immunity", Seminars in Immunopathology, vol. 32, No. 1, Jan. 30, 2010, pp. 79-90, XP55020185, Bethesda MD USA ISSN: 1863-2297, DOI: 10.1007/s00281-009-0191-2 abstract.

* cited by examiner

*Primary Examiner* — Rod P Swartz
(74) *Attorney, Agent, or Firm* — Rothwell, Figg, Ernst & Manbeck, P.C.

(57) ABSTRACT

The invention relates to methods and reagents for determining efficacy of vaccine, particularly of a tuberculosis vaccine.

15 Claims, 12 Drawing Sheets

DETERMINATION OF THE EFFICACY OF AN ANTI-MYCOBACTERIAL VACCINATION

CROSS REFERENCE TO RELATED APPLICATION

Figure 1:
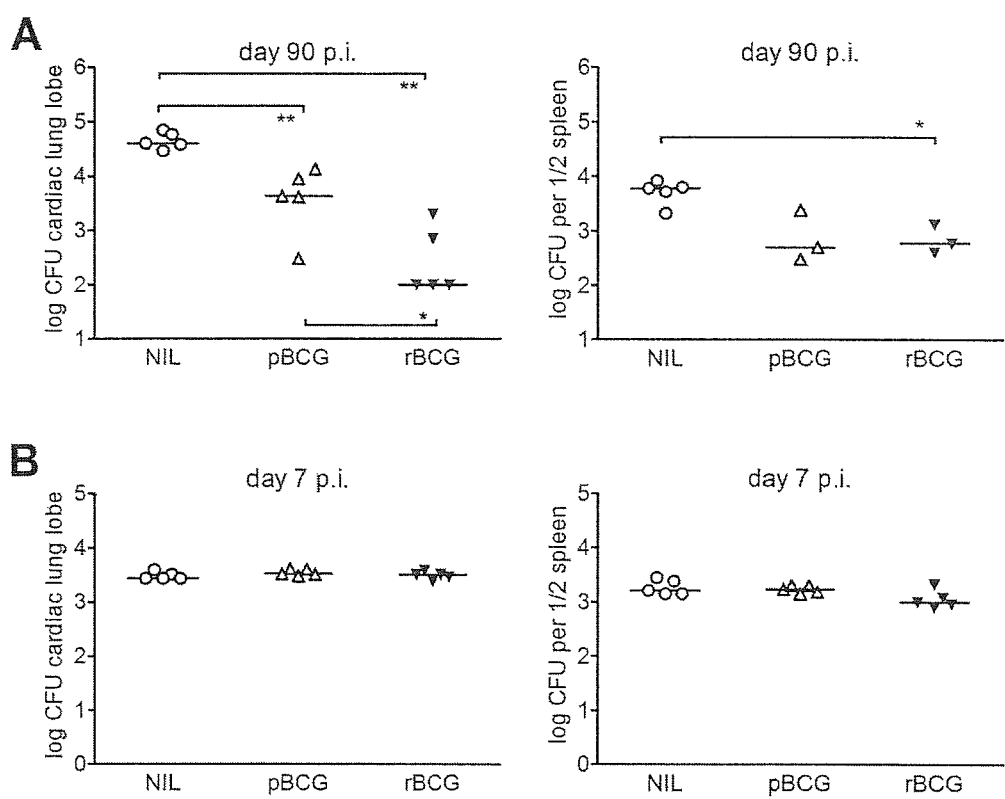

This application is a 35 U.S.C. 371 National Phase Entry Application from PCT/EP2011/073609, filed Dec. 21, 2011, which claims the benefit of U.S. Patent Application No. 61/425,442, filed Dec. 21, 2010, the disclosures of which are incorporated herein in their entirety by reference.

The invention relates to methods and reagents for determining efficacy of a vaccine, particularly of a tuberculosis vaccine.

Every year, up to 2 million people die from tuberculosis (TB) (1). The only available vaccine against TB is *Mycobacterium bovis* Bacillus Calmette-Guérin (BCG), which was used in humans for the first time in 1921 (2). To date, 4 billion doses of BCG have been administered, rendering it the most widely used human vaccine worldwide (3). Yet, we are still far from having achieved eradication of TB. BCG vaccination prevents tuberculous meningitis and miliary TB in infants (4). However, protection against other forms of TB, notably pulmonary TB in adolescents and adults is inconclusive as emphasized by a meta-analysis, which revealed protective efficacies ranging from 0-80% in adults (5). Therefore, new vaccines against TB are urgently needed. Currently, new vaccination strategies against TB in clinical trials include recombinant BCG to replace canonical BCG as well as subunit vaccines and non-replicating viral vector-based vaccines to booster BCG prime (6) (7).

The identification of immunologic mechanisms underlying protection can facilitate rational design of novel vaccination strategies for TB prevention. Moreover, this strategy could reveal biomarkers indicative for protective immunity that could reveal surrogate endpoints of clinical outcome in clinical TB vaccine efficacy trials, and thus reduce their duration as well as facilitate testing of larger numbers of vaccine candidates in parallel trials. Observational studies focusing on newly infected, healthy contacts of TB patients and on BCG-vaccinated infants have been initiated to define such biomarkers (8). Despite extensive research on the immune response to TB, the fundamental elements of protective memory have yet to be elucidated. After BCG vaccination, antigen-specific memory CD4 T cells are difficult to detect due to the paucity of immunodominant antigens. Currently, the most widely used biomarkers are based on elevated frequencies of CD4 T cells producing IFNγ. Increasing evidence questions the value of IFNγ as correlate of protection in TB (9,10). Undoubtedly IFNγ does play a crucial role in defense against *Mycobacterium tuberculosis* (MTB) (11), but determination of IFNγ alone can no longer be considered as a reliable marker of protective immunity.

A recombinant BCG strain expressing a phagolysosomal escape domain is described in WO99/101496, the content of which is herein incorporated by reference. The phagolysosomal escape domain enables the strain to escape from the phagosome of infected host cells by perforating the membrane of the phagosome. In order to provide an acidic phagosomal pH for optimal phagolysosomal escape activity, a urease-deficient recombinant strain was developed. This strain is disclosed in WO2004/094469, the content of which is herein incorporated.

A recombinant ΔureC Hly$^+$ rBCG (rBCG) strain expressing membrane-perforating listeriolysin (Hly) of *Listeria monocytogenes* and devoid of urease C induces superior protection against aerogenic challenge with MTB as compared to parental BCG (pBCG) in a preclinical model (12). This vaccine construct has successfully proven safety and immunogenicity in a phase I clinical trial (U.S. 61/384,375), the content of which is herein incorporated by reference.

In the present study, it is shown that rBCG and pBCG induce marked Th1 immune responses, whilst only rBCG elicits are profound Th17 response in addition. It was also observed earlier recruitment of antigen-specific T lymphocytes to the lung upon MTB infection of rBCG-vaccinated mice. These T cells produced abundant Th1 cytokines after restimulation. Superior protective efficacy of rBCG was apparently dependent on IL17. Elevated IL17 production after rBCG, but not pBCG vaccination, was also detected in healthy volunteers during a phase I clinical trial. Our findings identify a general immunologic pathway as a marker for improved vaccination strategies against TB that can also be explored by subunit vaccine candidates.

A subject-matter of the present invention is a method for determining efficacy of a vaccine, comprising determining the Th17 immune response in a vaccinated subject, wherein the presence of a Th17 immune response is indicative for protective immunity in said subject.

A further aspect of the present invention is a reagent kit for determining efficacy of a vaccine comprising at least one reagent for detecting a Th17 immune response.

In a preferred embodiment, the vaccine is a live vaccine, particularly a *Mycobacterium* cell. In an even more preferred embodiment, the vaccine is a recombinant *Mycobacterium* which comprises a recombinant nucleic acid molecule encoding a fusion polypeptide comprising (a) a domain capable of eliciting an immune response and (b) a phagolysosomal escape domain. The domain capable of eliciting an immune response is preferably an immunogenic peptide or polypeptide from a pathogen or an immunogenic fragment thereof. In a further embodiment, the vaccine is a subunit vaccine, i.e. a vaccine comprising a purified antigen from a pathogen or an immunogenic fragment thereof, particularly a recombinant antigen or an immunogenic fragment thereof. In a still further embodiment the vaccine is a vaccine based on an inactivated whole pathogen cell or cell fraction.

The *Mycobacterium* cell is preferably an *M. bovis* cell, an *M. tuberculosis* cell, particularly an attenuated *M. tuberculosis* cell or other Mycobacteria, e.g. *M. microti, M. smegmatis, M. canettii, M. marinum* or *M. fortuitum*. More preferably, the cell is a recombinant *M. bovis* (BCG) cell, particularly a recombinant *M. bovis* cell from strain Danish subtype Prague (43). In an especially preferred embodiment, the vaccine is a recombinant urease-deficient *Mycobacterium* cell. In an especially preferred embodiment the ureC sequence of the *Mycobacterium* cell is inactivated (ΔUrec), e.g. by constructing a suicide vector containing a ureC gene disrupted by a selection marker gene, transforming the target cell with the vector and screening for selection marker-positive cells having a urease negative phenotype. Most preferably, the cell is recombinant BCG strain Danish subtype Prague characterized as rBCG ΔUrec::Hly$^+$::Hyg$^+$.

The domain capable of eliciting an immune response is preferably selected from immunogenic peptides or polypeptides from *M. bovis* or *M. tuberculosis* or from immunogenic fragments thereof having a length of at least 6, preferably at least 8 amino acids, more preferably at least 9 amino acids and e.g. up to 20 amino acids. Specific examples for suitable antigens are Ag85B (p30) from *M. tuberculosis*, Ag85B (α-antigen) from *M. bovis* BCG, Ag85A from *M. tuberculosis* and ESAT-6 from *M. tuberculosis* and fragments thereof.

The vaccine is preferably a vaccine against mycobacterial infections, particularly pulmonary mycobacterial infections, more particularly tuberculosis.

According to the method of the invention, the Th17 immune response in a vaccinated subject is determined. The subject is preferably a mammal, e.g. a human. The determination is preferably carried out in a biological sample derived from said subject, wherein said sample comprises immune cells, particularly T cells and/or NK cells, more particularly antigen-specific T cells such as CD4 T cells. The sample may be a body fluid or tissue sample, e.g. a blood, serum or plasma sample or a sample from lung or spleen. Methods for collecting samples are well known in the art.

The method of the present invention requires a determination of the Th17 immune response. For this purpose it is preferred to restimulate the immune cells present in the sample in the subject to be analyzed with an immunogen and determining cytokine expression from said cells. The cells to be analyzed are preferably antigen-specific T cells, more preferably CD4 T cells. The immunogen for the restimulation corresponds to the immunogen present in the vaccine (the efficacy of which is to be determined). The immunogen may be present either in a form identical to the form present in the vaccine or in a different form. For example, when the vaccine comprises an immunogenic polypeptide, the immunogen in the restimulation step may comprise an immunogenic fragment thereof or vice versa. Preferably, the immunogen used for the restimulation step is a purified polypeptide or peptide. In order to test the efficacy of tuberculosis vaccines, particularly a live tuberculosis vaccine as described above, the immunogen may be advantageously a mycobacterial antigen, e.g. selected from PPD "Purified Protein Derivative", which is a glycerol extract of mycobacteria or Ag85A and Ag85B, as well as other mycobacterial antigens and immunogenic fragments thereof (such as described above).

Determination of the Th17 response according to the invention may comprise determining cells associated with the Th17 response, e.g. IL-17 producing cells, by means of surface markers and cytokines present in and/or secreted by said cells. Examples of surface markers are CD4, CD8, IL-23R, CCR4 and/or CCR6. Examples of cytokines present in and/or secreted by such cells are IL-17, IL-21, IL-22, IL-23, IFN-γ and combinations thereof. Preferably, the cytokine is IL-17. Such cells may be determined by cytological methods, e.g. by cell sorting techniques using immunological detection reagents such as antibodies specific for cell-surface markers and/or cytokines, which may carry a labelling, e.g. a fluorescence group.

More preferably, cells associated with a Th17 immune response are e.g. CD4 T cells producing and optionally secreting IL-17.

In a further embodiment the determination of the Th17 immune response comprises determining a cytokine secreted from Th17 immune response associated cells, e.g. IL-17. The cytokine may be determined by immunological methods using appropriate antibodies, e.g. antibodies directed against IL-17.

In the method of the invention, the Th17 immune response is determined at a suitable time after vaccination. For example, the immune response may be determined 20-50 days, particularly 25-35 days after vaccination.

The invention also refers to a reagent kit for determining efficacy of a vaccine, particularly for use in a method as described above. The reagent kit comprises an immunogen suitable for restimulating immune cells present in a sample from a subject which has been vaccinated. Further the reagent kit comprises at least one reagent suitable for detecting a Th17 immune response marker, as described above. The reagents may e.g. be selected from cytological and/or immunological detection reagents, e.g. antibodies against cell markers characteristic for Th17 immune response associated cells and/or an immunological reagent specific for cytokines associated with a Th17 immune response, particularly IL-17 and/or IL-22. The detection regions may carry detectable groups, e.g. fluorescence labelling groups.

Further, the invention is described in more detail by the following Figures and Examples.

FIGURE LEGENDS

FIG. 1: MTB burden in WT mice. S.c. immunization protects against infection with MTB 90 days p.i. (A). Bacterial burden is comparable between vaccinated and non-vaccinated groups day 7 p.i. (B). CFU determination in lung and spleen after aerosol infection with 400 CFU MTB. The cardiac lung lobe (approx. $71/10^{th}$ of the whole organ) or half a spleen was homogenized; the remaining material was used for in vitro restimulation assays. Statistical significance determined by Mann-Whitney test with two-tailed P values. *, P<0.05; **, P<0.01. Data are representative of three experiments with similar results.

Figure 2:
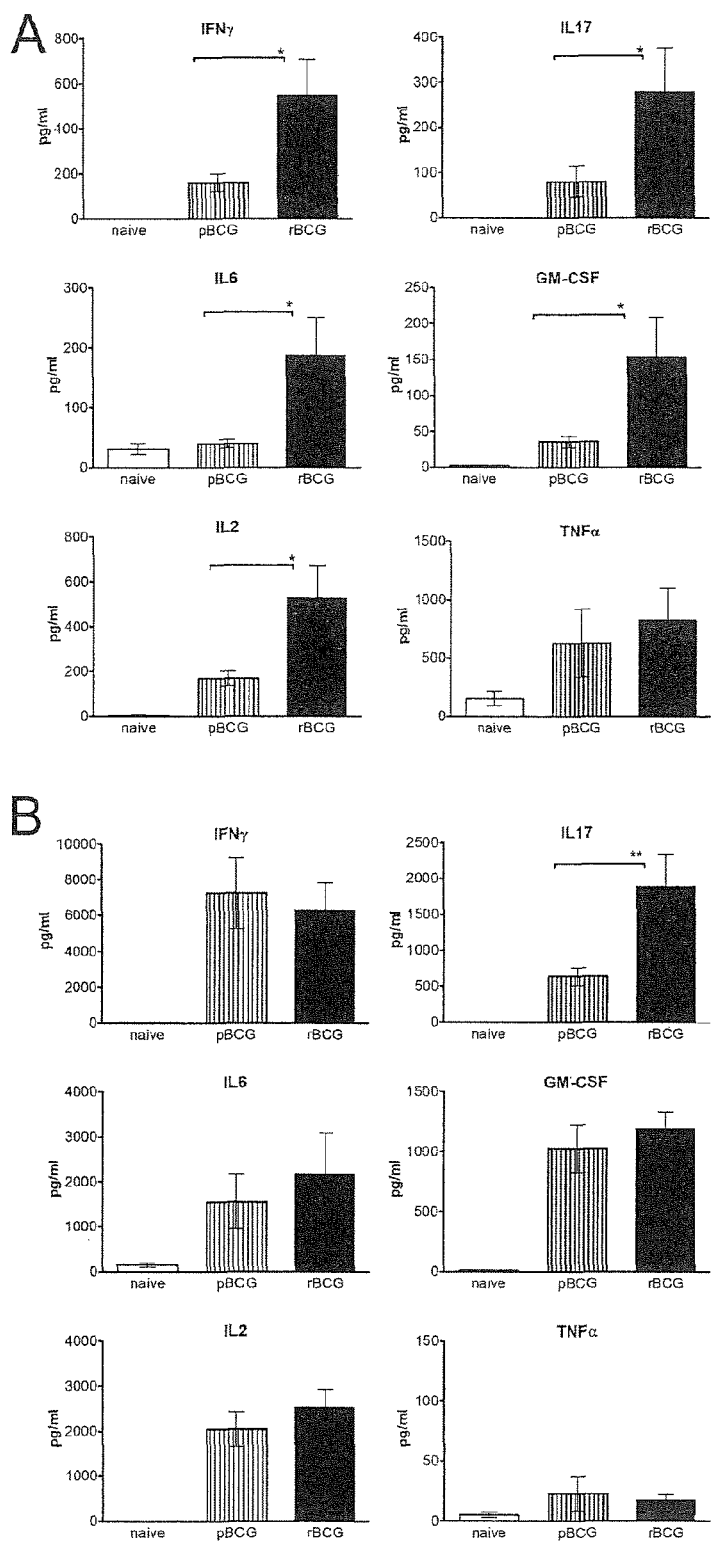

FIG. 2: Superior cytokine induction after rBCG over pBCG vaccination. Responses in lung (A) and spleen (B) 83 days after s.c. vaccination with rBCG or pBCG. A total of $2.5 \times 10^5$ (lung) or $2 \times 10^6$ cells (spleen) were restimulated with PPD for 20 hours and supernatants analyzed by multiplex assays. Cytokine concentrations are depicted as means±SEM of four independent experiments with three replicates each. Background cytokine production from medium controls was subtracted. ANOVA and Bonferroni Multiple Comparison Test were applied for statistical analysis. *, P<0.05; **, P<0.01.

Figure 3:
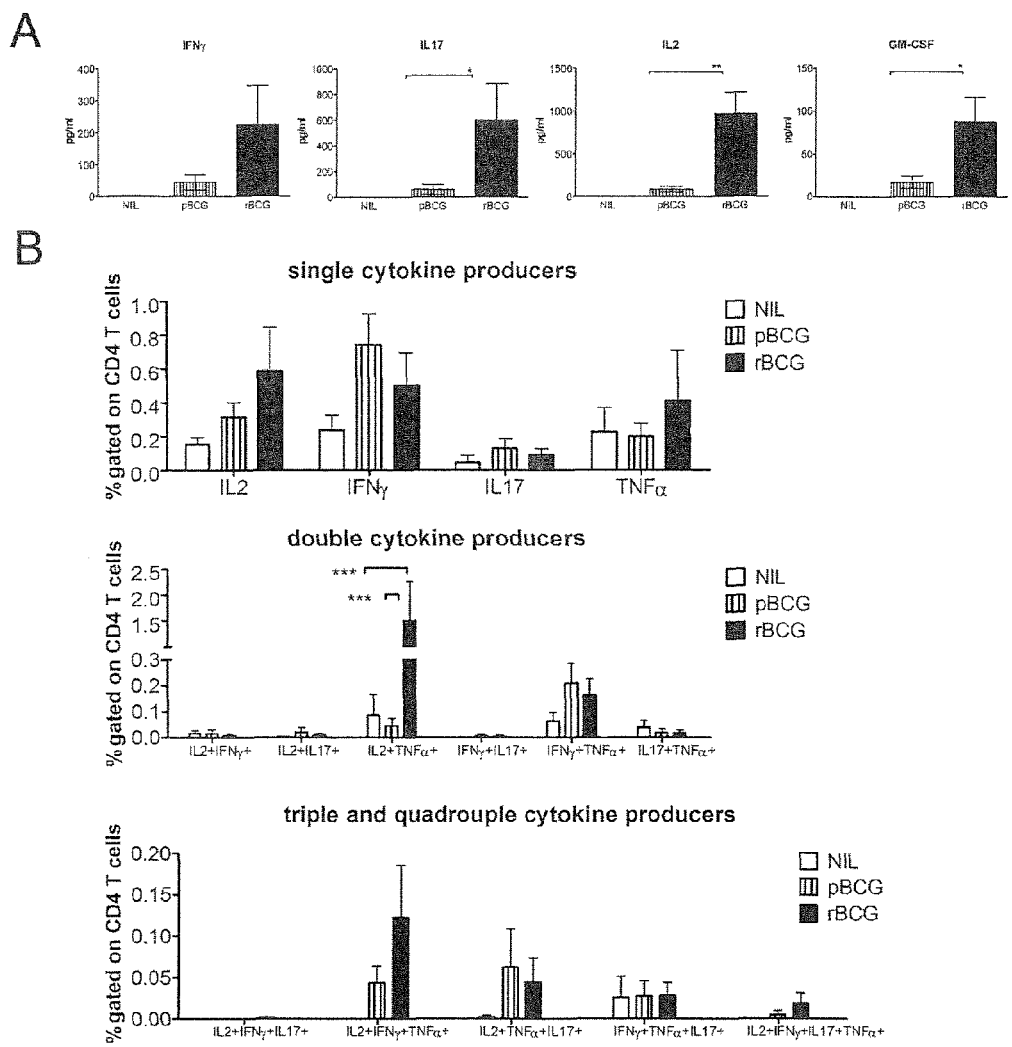

FIG. 3: Vaccination with rBCG accelerates recruitment of antigen-specific T cells to the lung upon aerosol infection with MTB. Cytokine secretion by lung cells 7 days after aerosol infection with 200-400 CFU MTB. A total of $2 \times 10^5$ cells were stimulated with PPD for 20 hours and supernatants analyzed by multiplex assay (A). Cytokine concentrations are depicted as mean±SEM of two independent experiments with three replicates each. Background cytokine production from medium controls was subtracted. Cells restimulated with PPD for 6 hours in the presence of Brefeldin A were analyzed by multicolor flow cytometry (B). Frequencies of responding CD4 T cells are depicted as means±SEM of three independent experiments with three replicates each. ANOVA and Bonferroni Multiple Comparison Test were applied for statistical analysis. *, P<0.05; , P<0.01; *, P<0.001.

Figure 4:
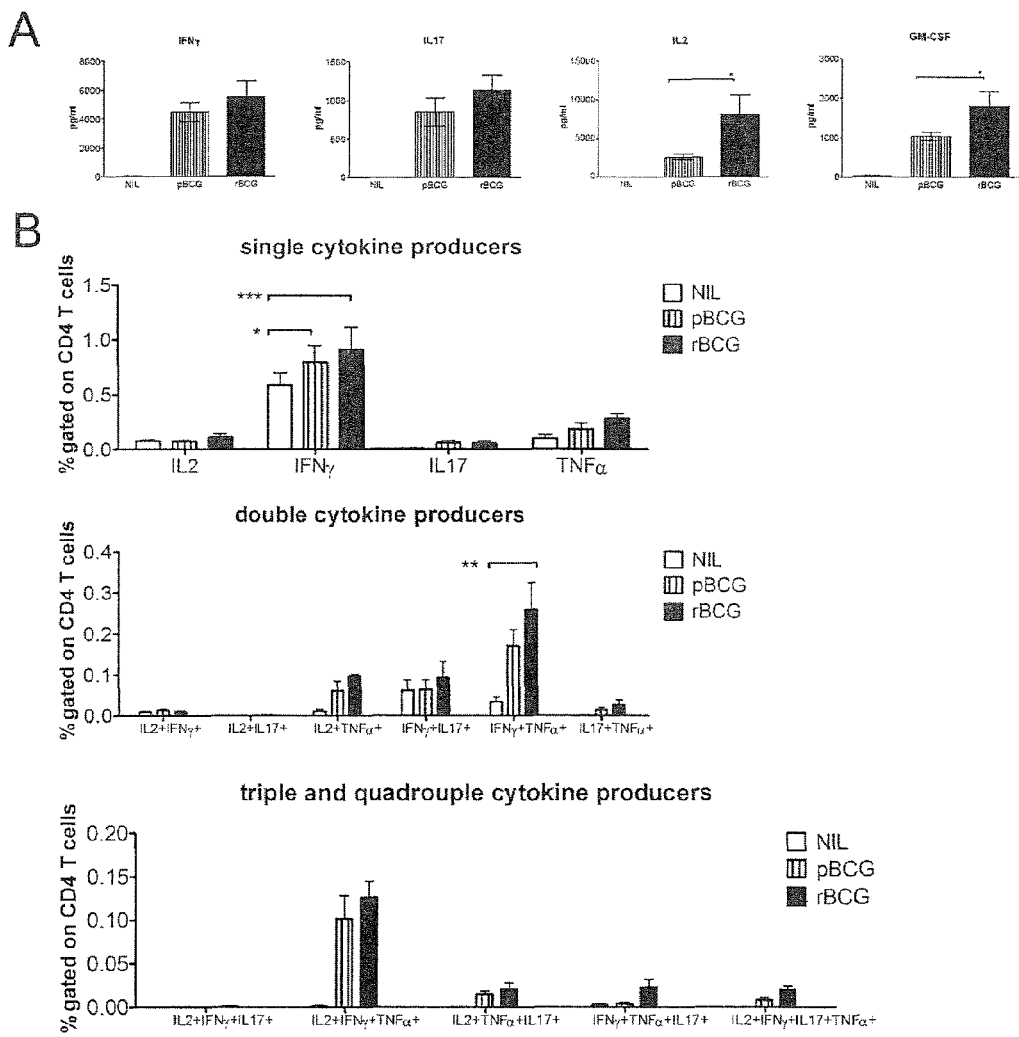

FIG. 4 Vaccination with rBCG increases PPD-specific responses in the spleen upon aerosol infection with MTB. Cytokine secretion by spleen cells 7 days after aerosol infection with 200-400 CFU MTB. A total of $2 \times 10^6$ cells were restimulated with PPD for 20 hours and supernatants analyzed by multiplex assays (A). Cytokine concentrations are depicted as means±SEM of four independent experiments with three replicates each. Background cytokine production from medium controls was subtracted. Cells restimulated with PPD for 6 hours in the presence of Brefeldin A were analyzed by multicolor flow cytometry (B). Frequencies of responding CD4 T cells are depicted as mean±SEM of three independent experiments with three replicates each. ANOVA and Bonferroni Multiple Comparison Test were applied for statistical analysis. *, P<0.05; , P<0.01; *, P<0.001.

Figure 5:
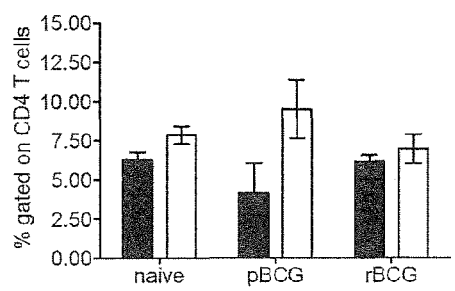
Figure 5:
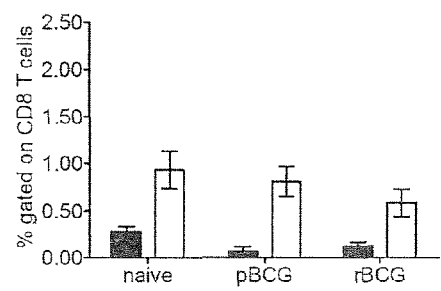
Figure 5:
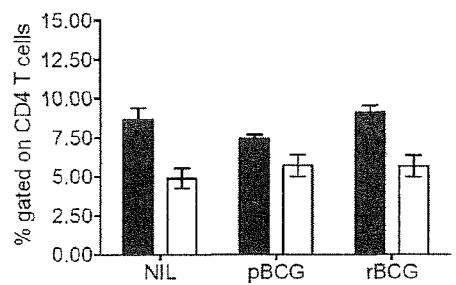
Figure 5:
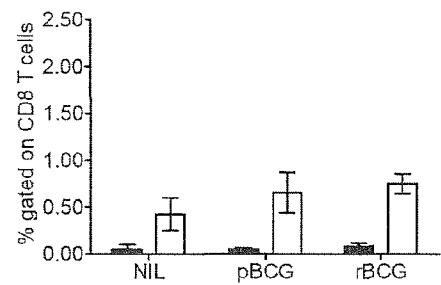
Figure 5:
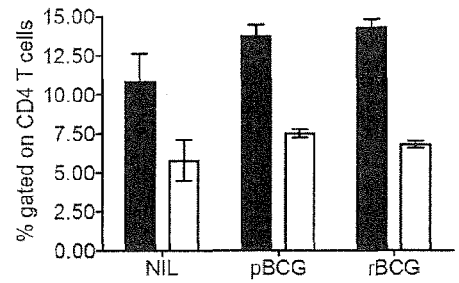
Figure 5:
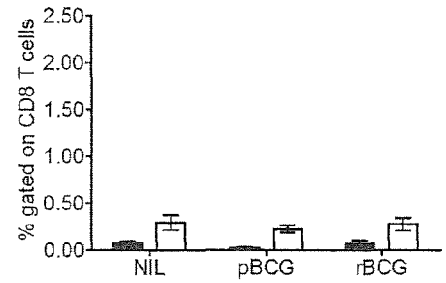

FIG. 5: Vaccination with pBCG or rBCG does not lead to significant changes in Treg cell populations. Treg cells in the spleen after s.c. immunization with rBCG or pBCG. Black bars represent CD25+FoxP3+ and white bars CD25−FoxP3+ cells. Frequencies of CD4 T cells and CD8 Treg cells 83 days after immunization (A and B) as well as 7 days (C and D) or 90 days (E and F) after aerosol infection with 200-400 CFU MTB. Three mice per group, depicted as mean±SEM. Data are representative of three independent experiments with similar results.

Figure 6:
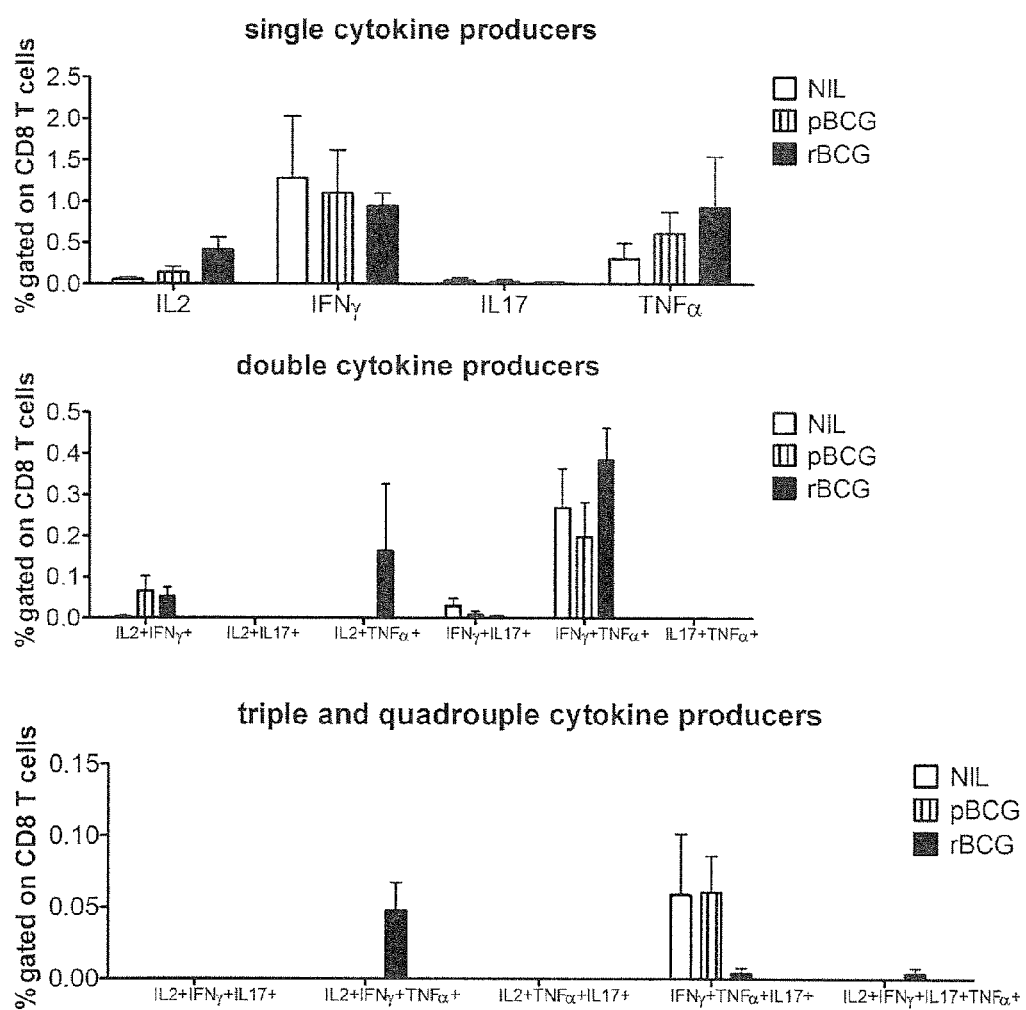

FIG. 6: Frequencies of cytokine producing CD8 T cells in the lung after vaccination and subsequent aerosol infection with MTB. Cytokine secretion 7 days after aerosol infection with 200-400 CFU MTB. Cells restimulated with PPD for 6 hours in the presence of Brefeldin A were analyzed by multicolor flow cytometry. Frequencies of responding CD8 T cells are depicted as mean±SEM of two independent experiments with three replicates each. ANOVA and Bonferroni Multiple Comparison Test were applied for statistical analysis.

Figure 7:
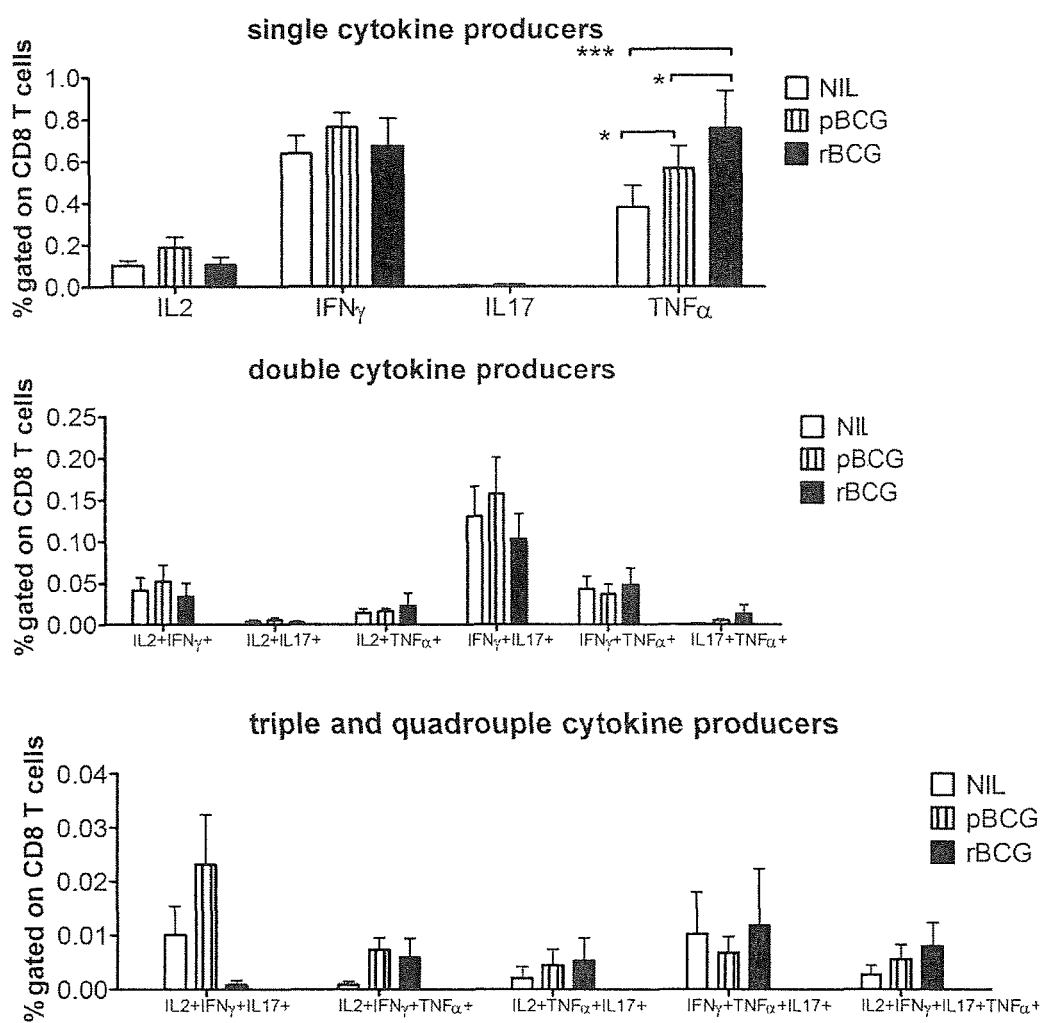

FIG. 7: Frequencies of cytokine producing CD8 T cells in the spleen after vaccination and subsequent aerosol infection with MTB. Cytokine secretion 7 days after aerosol infection with 200-400 CFU MTB. Cells restimulated with PPD for 6 hours in the presence of Brefeldin A were analyzed by multicolor flow cytometry. Frequencies of responding CD8 T cells are depicted as mean±SEM of four independent experiments with three replicates each. ANOVA and Bonferroni Multiple Comparison Test were applied for statistical analysis. *, $P<0.05$; , $P<0.01$; *, $P<0.001$.

Figure 8:
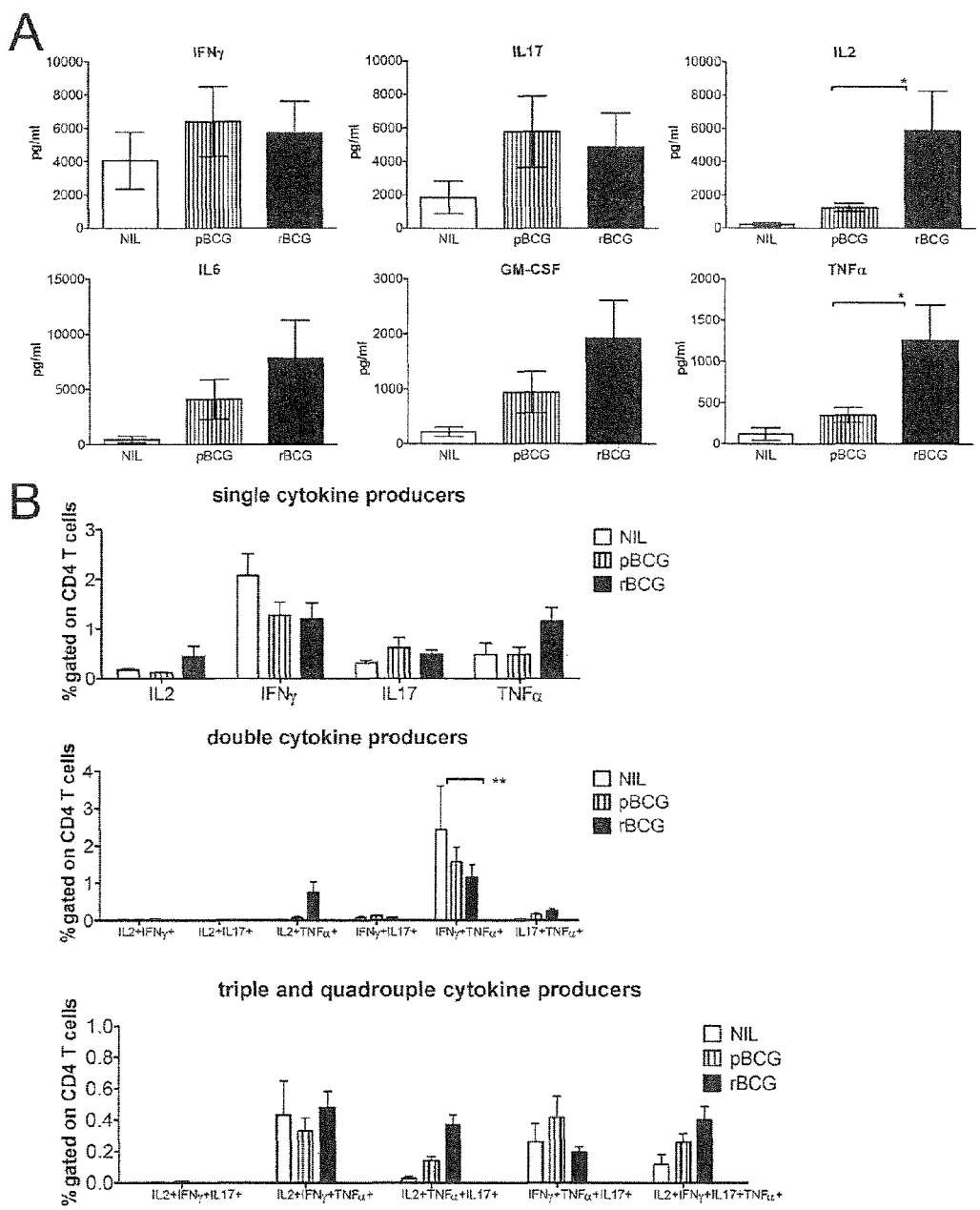

FIG. 8: Immune responses in the lung during persistent MTB infection in rBCG-vaccinated mice. Cytokine secretion by lung cells 90 days after aerosol infection with 200-400 CFU MTB. Cells were restimulated with PPD for 20 hours and supernatants analyzed by multiplex assays (A). Cytokine concentrations are depicted as means±SEM of two independent experiments with three replicates each. Background cytokine production from medium controls was subtracted. Cells restimulated with PPD for 6 hours in the presence of Brefeldin A were analyzed by multicolor flow cytometry (B). Frequencies of responding CD4 T cells are depicted as mean±SEM of two independent experiments with three replicates each. ANOVA and Bonferroni Multiple Comparison Test were applied for statistical analysis. *, $P<0.05$; **, $P<0.01$.

Figure 9:
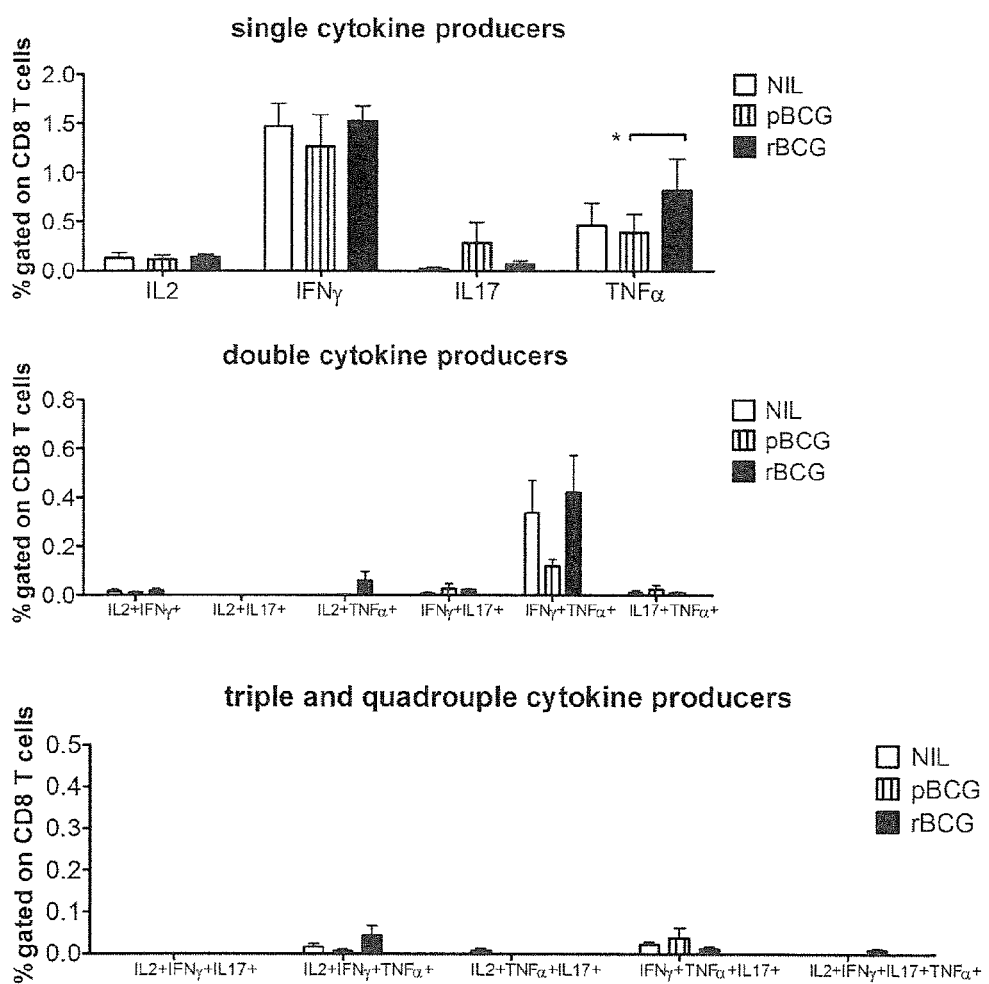

FIG. 9: Frequencies of cytokine producing CD8 T cells after vaccination and subsequent aerosol infection with MTB. Cytokine secretion by cells isolated from the lung 90 days after aerosol infection with 200-400 CFU MTB. Cells restimulated with PPD for 6 hours in the presence of Brefeldin A were analyzed by multicolor flow cytometry. Frequencies of responding CD8 T cells are depicted as mean±SEM of two independent experiments with three replicates each. ANOVA and Bonferroni Multiple Comparison Test were applied for statistical analysis. *, $P<0.05$.

Figure 10:
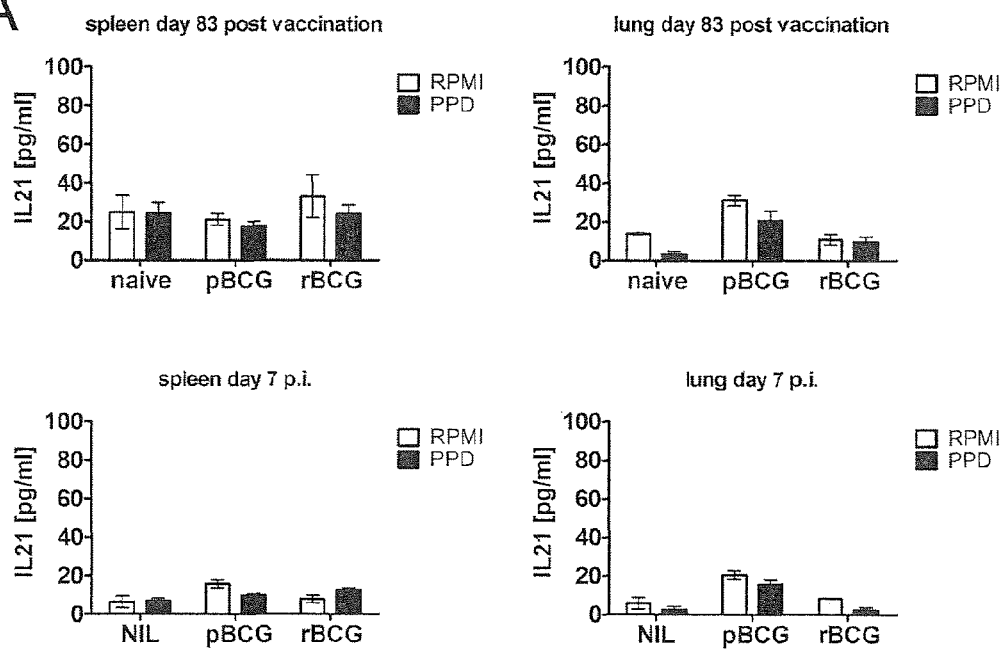
Figure 10:
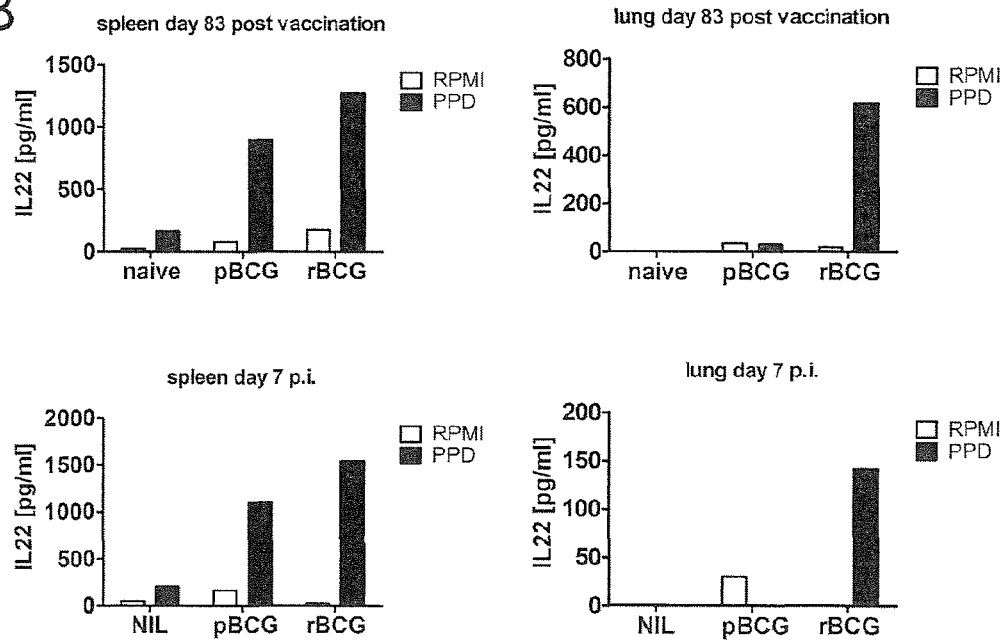

FIG. 10: Vaccination induces IL22 but not IL21 production. IL21 (A) and IL22 (B) secretion by cells from spleens ($2\times10^6$ cells) or lungs ($2\times10^5$ cells) of mice 83 days after vaccination and subsequent aerosol infection with 200-400 CFU MTB. IL21 concentrations measured from three samples per group, mean±SEM depicted. For IL22 samples from one group were pooled. Data are representative of two (day 83 post vaccination) and five (day 7 p.i.) similar experiments. Cells were restimulated with PPD for 20 hours and supernatants analyzed by ELISA.

Figure 11:
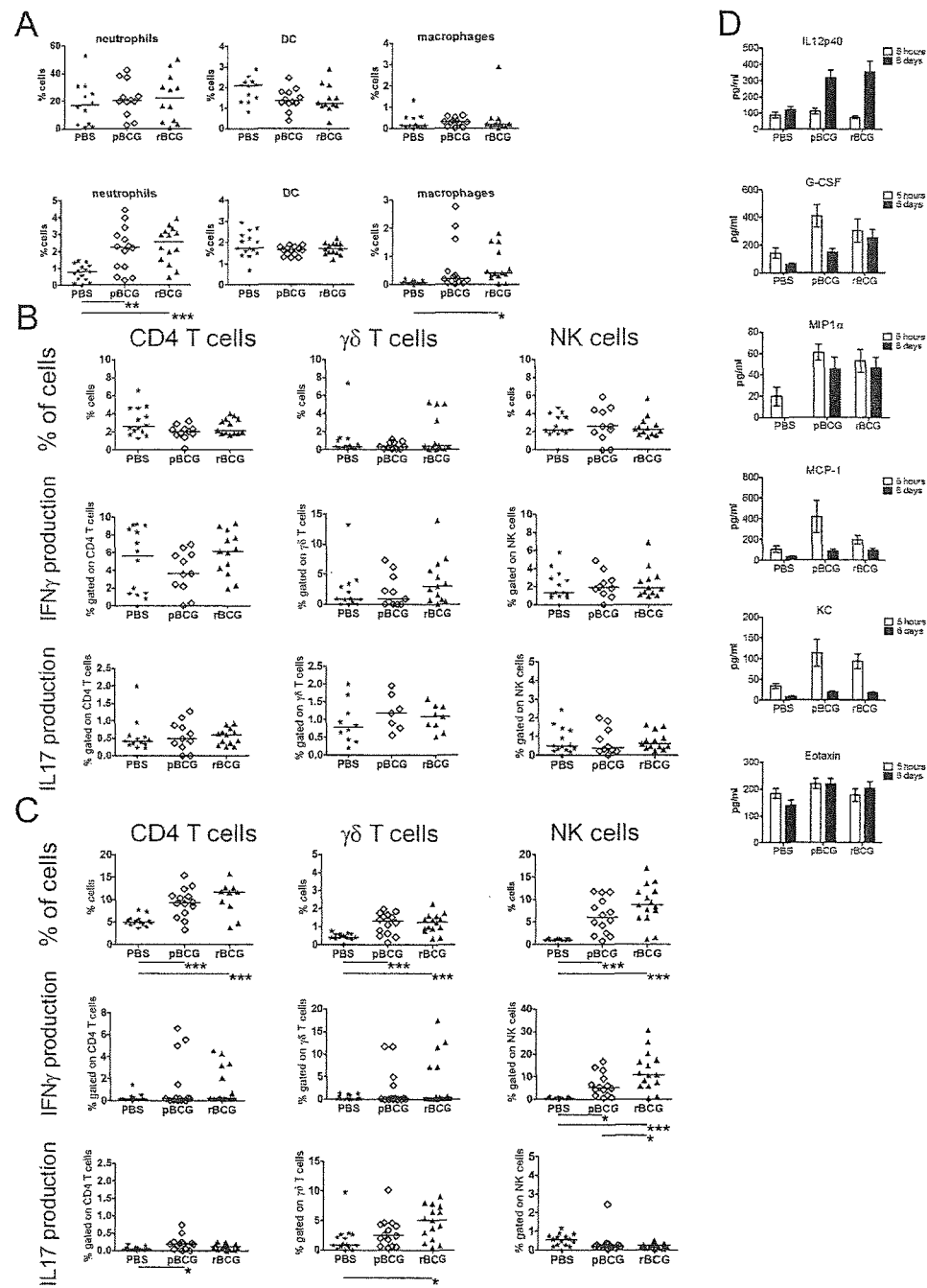

FIG. 11: rBCG causes increased recruitment of γδT cells and NK cells without significantly altering APC populations. Cells recruited to the peritoneal cavity on administration of $10^6$ CFU of rBCG or pBCG i.p. Analysis of cell populations in peritoneal lavage fluid by flow cytometry. APC recruited to the peritoneum 5 hours (upper panel) and 6 days (lower panel) after i.p. administration of rBCG or pBCG (A). ICS of T cell populations 5 hours after injection (B). Cells were stimulated with αCD3/αCD28 antibodies for 18 hours in the presence of Brefeldin A. ICS of T cell populations 6 days after administration (C). Cells were restimulated with PPD for 18 hours in the presence of Brefeldin A. Data presented as summary of three independent experiments with five mice per group. Horizontal line indicates median. ANOVA and Bonferroni Multiple Comparison Test were applied for statistical analysis. *, $P<0.05$; **, $P<0.01$. Cytokines and chemokines detected in peritoneal lavage fluid analyzed by multiplex assay (D) depicted as mean concentrations±SEM.

Figure 12:
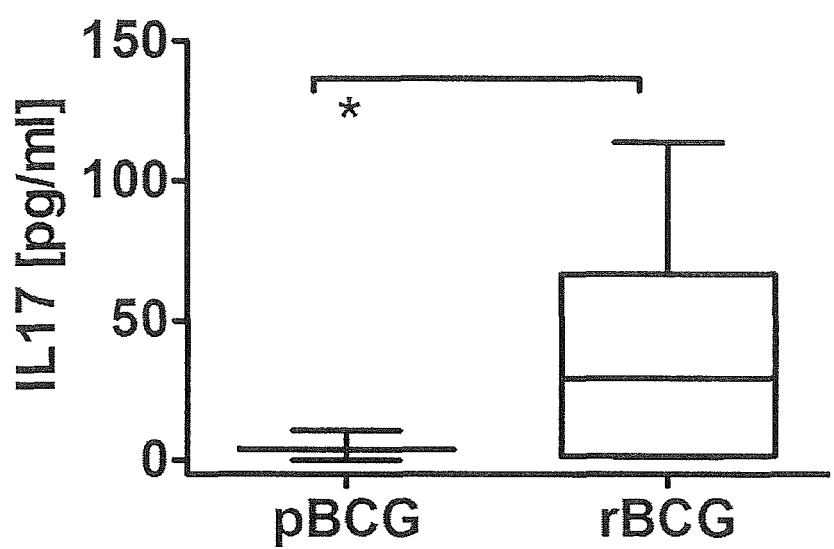

FIG. 12: rBCG induces IL17 in human PBMCs from healthy volunteers of a phase I clinical trial. IL17 production by human PBMCs isolated from healthy human volunteers of a phase I clinical study. A total of $5\times10^5$ cells isolated 29 days post vaccination with rBCG or pBCG, were restimulated with PPD for 20 hours and supernatants analyzed by multiplex assay. Statistical significance determined by Mann-Whitney test with one-tailed P value and Welch's correction. *, $P<0.05$; n=3 for pBCG and n=7 for rBCG.

EXAMPLE

Materials and Methods

Mice

Female BALB/c mice were bred at the Bundesinstitut für Risikobewertung (BfR) in Berlin. Mice were 6-8 weeks of age at the beginning of the experiments and kept under specific pathogen-free (SPF) conditions. Animal experiments were conducted with the approval of the Landesamt für Gesundheit und Soziales (LAGeSo, Berlin, Germany).

Bacteria

The MTB H37Rv and the pBCG and rBCG strains used were described previously (12). Bacteria were grown in Middlebrook 7H9 broth supplemented with glycerol, 0.05% Tween 80 and ADC. Mid-logarithmic cultures were harvested and stored at −80° C. until use. All stocks were titrated prior to use. Single cell bacterial suspensions were obtained by repeated transfer through a syringe with a 27 G needle.

Vaccination and MTB Infection pBCG or rBCG ($10^6$ CFU) were administered subcutaneously (s.c.) in close proximity to the tail base. Aerogenic infection of mice with MTB was performed using a Glas-Col inhalation exposure system. Bacterial burdens were assessed by mechanical disruption of aseptically removed organs in PBS 0.5% v/v Tween 80 and plating serial dilutions onto Middlebrook 7H11 agar plates supplemented with OADC. After 3 weeks, MTB colonies were counted. Statistical significance of results was determined by Mann-Whitney test with two-tailed p-values for non-parametric data using GraphPad Prism 5.0.

Cell Isolation, Stimulations and Flow Cytometry

Cells were purified as previously described (42). Experimental groups comprised five mice. Two spleens or lungs were pooled and one sample processed individually, resulting in three samples per group of five mice for subsequent stimulations. Cells were stimulated with 50 μg/ml PPD (SSI, Copenhagen, Denmark) for 20 hours for cytokine analysis by multiplex assay or for 6 hours in the presence of 25 μg/ml Brefeldin A for intracellular cytokine staining (ICS). The following antibodies were used: CD4 (RM4-5), IFNγ (XMG-1.2), IL2 (JES6-5H4), Ly6G/C (RB6-8C5), CD11b (M1/70), γδ-TCR (GL-3), FoxP3 staining set and CD49b (cloneDX5)

all eBioscience. CD8α (YTS169), TNF-α (XT22), CD16/CD32 (2.4G2), F4/80 (CI:A3-1) and CD11c (N418) were purified from hybridoma supernatants and fluorescently labeled in house. IL-17 (TC11-18H10) was obtained from BD Biosciences. Cells were analyzed using a FACSCanto II or LSRII flow cytometer and FACSDiva software (BD Biosciences). Cytokines were measured using the Bio-Plex Mouse Th1/Th2, IL17 and IL6 bead-based immunoassays from Bio-Rad according to manufacturer's instructions. IL21 and IL22 were measured by ELISA from R&D systems. Human IL17 was detected with a Milliplex 42-plex assay from Millipore.

Peritoneal Lavage pBCG or rBCG were freshly prepared from mid-logarithmic cultures. Bacteria were washed three times with PBS and concentration determined by measuring optical density at 580 nm. Administration of $10^6$ CFU was performed intraperitoneally. Recruited cells were obtained from the peritoneal cavity 5 hours or 6 days later by injection of 5 ml PBS and analyzed by flow cytometry. Cytokines and chemokines in lavage fluid were determined using the Bio-Plex Mouse Cytokine 23-plex kit from Bio-Rad.

Results

Th1/Th17 Responses after rBCG and pBCG Vaccination

In an attempt to elucidate immune mechanisms relevant to TB vaccine efficacy, we compared immune responses to rBCG and pBCG in mice. Superior protective efficacy of rBCG had been originally determined after i.v. immunization (12). Here we show that s.c. administration of rBCG induced comparable levels of protection and retained its superior efficacy over pBCG (FIG. 1A). Next, we analyzed long-term memory responses in lungs and spleens of mice 83 days after s.c. vaccination with rBCG or pBCG. Cells were restimulated with PPD and supernatants analyzed by multiplex assays for cytokines. Immunization with rBCG induced significantly higher cytokine production by cells isolated from the lung as compared to pBCG (FIG. 2A). These included IFNγ, IL2, IL6, and GM-CSF. In contrast, type 2 cytokines IL4, IL5 and IL10 were not increased above background levels (data not shown). Intriguingly, approximately 3-fold higher IL17 concentrations were produced by lung cells from rBCG-vaccinated mice. Note that only few cells could be isolated from the lungs of uninfected mice. Consequently, overall cytokine concentrations were lower than in spleen where 10-fold higher cell densities per well could be used for stimulation (FIG. 2B). In spleens, both vaccines elicited equally strong Th1 responses as reflected by comparable concentrations of IL2, IL6, IFNγ and GM-CSF. Yet, spleen cells from rBCG-vaccinated mice produced significantly more IL17 upon restimulation with PPD as compared to pBCG-vaccinated animals. Thus, immunization with rBCG, but not pBCG, induced concomitant and strong Th1 and Th17 responses in lungs and spleens, which were sustained for prolonged periods of time.

Accelerated Recruitment of MTB-Specific T Cells Upon Infection with Virulent MTB in rBCG-Vaccinated Mice Th17 cells have been linked to improved immune surveillance (13). We compared antigen-specific T cell responses in vaccinated animals upon aerosol infection with virulent MTB, in lungs and spleens 7 days post infection. Marked IFNγ, IL17, IL2 and GM-CSF production by lung cells from rBCG-vaccinated mice was detected 20 hours after restimulation with PPD (FIG. 3A) or Ag85A peptides (data not shown). In contrast, these cytokines were barely secreted by cells from pBCG-vaccinated mice. In non-vaccinated animals infected with MTB, cytokine production was below detection limit, in agreement with previous reports that MTB-specific T cells do not appear before 3 weeks after MTB infection (13). The type 2 cytokines IL4, IL5 and IL10 were not detected and TNFα, IL12p70 and IL6 were only barely above background levels at this early timepoint post MTB challenge (data not shown).

We determined cytokine production by lung T cells by flow cytometry 7 days after MTB infection (FIG. 3B). Cells were stimulated with PPD for 6 hours followed by intracellular cytokine staining for IL2, IL17, IFNγ and TNFα. In non-vaccinated controls a small proportion of CD4 T cells produced IL2, TNFα or IFNγ. In vaccinated mice, CD4 T cells secreted IL2, IFNγ, TNFα and also IL17. Frequencies of single cytokine producing cells were highest, albeit not significant, in the rBCG group. In vaccinated animals we detected multifunctional T cells implicated in protective immunity (14). Multiple cytokine-producing T cells were predominantly IL2$^+$TNFα$^+$ double producers and significantly increased upon rBCG vaccination. Triple-producer cells were almost exclusively IL2$^+$IFNγ$^+$TNFα$^+$ and slightly increased in rBCG compared to pBCG-vaccinated mice. Also, IL2$^+$TNFα$^+$IFNγ$^+$IL17$^+$ quadruple-positive cells exclusively appeared in the rBCG group albeit at very low frequencies.

In principle, splenic T cells produced similar cytokine patterns as pulmonary T cells (FIG. 4). IL2 and GM-CSF production was significantly higher in the rBCG-vaccinated animals as compared to the pBCG group and below detection level in non-vaccinated controls, even though in non-vaccinated controls, a small percentage of CD4 T cells produced IFNγ. In sum, vaccination with either pBCG or rBCG induced CD4 T cells secreting IFNγ and TNFα with higher frequencies of single and multi-producers in rBCG-vaccinated mice as compared to the pBCG group.

At 7 days p.i. CD4 T cells were the main cytokine producers; CD8 cytokine producers were detected with lower frequencies in the lung (FIG. 6) and spleen (FIG. 7) albeit with similar patterns. It is of note that significantly higher frequencies of TNFα-single producing CD8 T cells were detected in the rBCG group.

Differential cytokine production and frequencies of producer cells were not due to different bacterial burdens at this early timepoint after infection, as confirmed by comparable colony forming unit (CFU) numbers in lungs and spleens (FIG. 1B). Total numbers of Treg cells increased upon infection to a comparable degree in the two vaccinated groups (FIG. 5).

Vaccination with rBCG Confers Potent Immune Responses During Persistent Infection We analyzed MTB-specific immune responses 90 days p.i. when lung bacterial burdens were approximately 10-fold lower in rBCG-immunized animals as compared to the pBCG group and 100-fold lower as compared to the non-vaccinated control group. Cells from lungs of vaccinated mice and untreated controls were restimulated with PPD for 20 hours and cytokine concentrations measured by multiplex assays (FIG. 8A). Cytokines detected upon restimulation were predominantly of type 1. However, we could not detect differences in IFNγ or IL17 between the vaccinated groups during persistent infection. In contrast, amounts of IL2, IL6, GM-CSF and TNFα were higher in rBCG-vaccinated mice. In all groups, IL4 and IL5 were below detection limit and some IL12p70 and IL10 were measured (data not shown). Additionally, analysis of lung cells by multicolor flow cytometry revealed predominantly cytokine-producing CD4 T cells during persistent infection (FIG. 8B). CD4 T cells secreting only IFNγ were detected in all groups with similar frequencies. Upon vaccination, CD4 T cells producing IL2, IFNγ, TNFα or IL17 in different combinations could be detected as well. Intriguingly, frequencies of responding CD4 T cells did not differ significantly between rBCG and pBCG vaccination despite higher concentrations of IL2 and TNFα in supernatants. We assume that both vaccines increased frequencies of antigen-specific CD4 T cells in the lung during persistent MTB infection with rBCG-induced T cells becoming more potent cytokine producers. CD8 T cells almost exclusively secreted IFNγ with comparable frequencies in all groups whereas significantly higher single TNFα-producing CD8 T cells were detected in the rBCG group. Multifunctional CD8 T cells appeared barely above background (FIG. 9).

Vaccination Causes IL22 but not IL21 Production

Th17 cells can produce additional effector cytokines such as IL21 (15) and IL22 (16). IL22 producing cells have been identified in TB patients, but these seem distinct from IL17 producing cells (17). We did not detect IL21 after stimulation with PPD of spleen or lung cells from vaccinated and subsequently MTB-infected mice (FIG. 10A). IL22 was produced at elevated concentrations by splenocytes stimulated with PPD for 20 hours (FIG. 10B) in rBCG-immunized mice but did not further increase early after infection with MTB. IL22 production by lung cells was only observed in the rBCG-vaccinated group and declined after aerosol MTB infection.

Intraperitoneal rBCG Causes Increased Recruitment of γδ T Cells and NK Cells without Significantly Altering APC Populations We wanted to define the mechanisms underlying preferential Th17 cell induction after immunization with rBCG. To this end, rBCG and pBCG were administered i.p., immigrant cells isolated from the peritoneal cavity 5 hours or 6 days after administration and analyzed by flow cytometry (FIG. 11A). Neutrophils (defined as $Gr1^{HI}$, $CD11b^{HI}$, $MHCII^-$, $CD11c^-$) rapidly entered the peritoneal cavity and remained elevated at day 6 p.i. in pBCG and rBCG groups to the same extent. Frequencies of resident peritoneal macrophages (defined as $CD11b^{HI}$, $F4/80^{HI}$, $Gr1^-$, $MHCII^{HI}$, $CD11c^-$) and dendritic cells ($CD11c^+$, $CD11b^{LO}$, $Gr1^-$) remained unchanged at low percentages. In sum, no significant differences were detectable between rBCG and pBCG groups. Peritoneal cells harvested 5 hours after vaccination were subjected to polyclonal stimulation (FIG. 11B) with αCD3/αCD28 antibodies. Frequencies of CD4 T cells and NK cells were comparable between all groups as were IFNγ and IL17 production. Six days after administration, these cells increased numerically and reached highest frequencies in the rBCG group (FIG. 11C). PPD was used for re-stimulation of cells at the 6 day timepoint. CD4 T cells did not produce appreciable amounts of IFNγ or IL17, whilst a substantial proportion of NK cells produced IFNγ after rBCG administration. γδ T cells have been identified as a major source of early IL17 in TB (18). Increased, albeit not significant, proportions of γδ T cells producing IFNγ were identified 5 hours post-injection with rBCG. This cell population further increased and markedly higher frequencies of γδ T cells producing IL17 were detected in the rBCG group 6 days after injection. CD8 T cells were not detected in the peritoneum in any of the groups. We analyzed cytokines and chemokines present in the peritoneal cavity by multiplex assay of peritoneal lavage fluid (FIG. 11D). MCP-1, MIP1α, G-CSF and KC were rapidly increased upon injection; levels of Eotaxin remained unchanged and IL12p40 was detected in higher concentrations after 6 days. IL12p70, IFNγ, IL1a, IL2, IL3, IL4, IL5, IL10, IL17, GM-CSF, and TNFα concentrations were below detection limit whereas IL1β, IL6, IL9, IL13, MIP1β and RANTES could be measured but production was comparable between rBCG and pBCG. Thus, rBCG and pBCG induced recruitment of APC as well as chemokine and cytokine production at the site of administration to a similar extent. Intriguingly, proportions of γδ T cells secreting IL17 and NK cells producing IFNγ were most abundant after rBCG administration.

Vaccination with rBCG Generates IL17-Producing Cells in Humans

Last, we analyzed PBMCs from healthy human volunteers of a phase I clinical trial to interrogate whether IL17 production was increased in rBCG-vaccinated study participants. Blood from volunteers was taken 29 days after immunization with rBCG or pBCG and PBMCs isolated and frozen. PBMCs were thawed and rested over night, followed by 20-hour restimulation with PPD. Cytokine production was analyzed by multiplex assays. IL17 production was exclusively detected in PBMCs from study participants immunized with rBCG (FIG. 12). Note that a limited number of samples was available.

Discussion

The identification of immune markers of protection is crucial for rational design of novel TB vaccines. These markers could also establish the basis for definition of surrogate markers to predict endpoints of clinical outcome in TB vaccine efficacy trials and thus provide guidelines for improvement of current vaccine candidates. The importance of key cytokines which activate macrophage antimycobacterial capacities including IFNγ (21) and TNFα (22), and the necessity for IL2 in the expansion of memory cells (23) are well established and thus commonly used to monitor TB vaccine trials.

In an attempt to identify biomarkers of vaccine efficacy, we compared long-term memory immune responses elicited by rBCG proven to confer superior protection over its parental strain, pBCG. Responses differed in both quantitative and qualitative terms. We detected increased abundance of type 1 cytokines as well as IL17 following vaccination with rBCG in the lung (FIG. 2A). Analysis of vaccine-induced immune responses in lung is obviously not feasible in the context of clinical trials. Therefore, we also analyzed systemic long-term memory responses (FIG. 2B). Intriguingly, comparable concentrations of type-1 directing cytokines were detected in the pBCG and rBCG groups. In contrast, IL17 production by splenocytes was significantly elevated upon rBCG vaccination. Thus, we conclude that IL17, rather than IFNγ or IL2 qualifies as a marker of superior protection induced by rBCG.

Th17 cells contribute to antimicrobial defense by attracting and activating neutrophils (24) which are among the first cells to be recruited in response to IL17. It has been shown that IL17 is dispensable during primary MTB infection (25,26), but gains importance in memory responses (13). In addition, recent reports on the expression of CCR6 on human Th17 cells (27,28) point to a positive feedback loop, because CCR6 is the receptor for CCL20 produced by neutrophils (29) and CCL20-CCR6 has been implicated in immunopathogenisis of TB (30). Thus, Th17 cells could facilitate accelerated recruitment of antigen-specific memory T cells to the sites of bacterial residence. By analyzing vaccine-induced immune responses 7 days after aerosol infection with MTB, we show that vaccination with rBCG indeed lead to accelerated recruitment of effector cells to the sites of bacterial replication. We observed increased frequencies of antigen-specific CD4 T cells and elevated production of IL2, IL17, IFNγ and GM-CSF by lung (FIG. 3) and spleen cells (FIG. 4).

Multifunctional CD4 T cells co-producing IL2, IFNγ and TNFα were first implicated in successful vaccination strategies against *Leishmania major* (14) and later also against MTB (31). Recently, these polyfunctional CD4 T cells were also detected in clinical TB vaccine trials (32,33). We detected polyfunctional CD4 T cells upon rBCG and pBCG vaccination and subsequent infection (FIGS. 3 and 4); however the composition of cytokines (IL2, IL17, IFNγ and TNFα) in double- and triple-producers varied considerably between experiments as well as individual animals. If multifunctional cells were a true correlate of protection, then their overall frequencies, which were higher in the rBCG group, rather than their composition, seem most relevant.

Why did rBCG induce a Th17 response? Immunization with rBCG and pBCG caused recruitment of APC as well as chemokine and cytokine producers to a similar extent. Intriguingly, proportions of γδ T cells secreting IL17 and NK cells producing IFNγ were highly abundant after rBCG vaccination. This is consistent with reports showing that IL17 can be rapidly produced by γδ T cells (34,18) as well as NKT cells (35). NK cells, which were also increased upon vaccination with rBCG, are an important source of early IFNγ. We have already shown that different molecular components released from rBCG reside in the cytosol of infected macrophages (12). Nod-2 is an important cytosolic PRR and its engangement has been linked to the development of Th17 memory T cell responses (19).

Apoptosis induced during bacterial infection induces Th17 cells (36). We have obtained evidence that rBCG induces increased apoptosis compared to pBCG (12), which could further contribute to increased development of Th17 cells. Activation of inflammasomes could also contribute to Th17 memory responses via production of IL1β (37). NLRP3 for example has been found to sense the presence of listeriolysin through changes in ATP levels (38). Thus, induction of Th17 cells upon rBCG vaccination might require a complex interplay of intracellular stimuli and increased apoptosis.

Th17 cells are considered instrumental in inflammatory and autoimmune diseases such as collagen-induced arthritis (39), EAE (40, 39) and allergic airway hypersensitivity (41, 39) rather than being beneficial for successful vaccination. This pathogenic role is usually associated with development of a profound IL21-mediated inflammatory response. We never detected IL21 after vaccination and subsequent MTB infection above background levels in any experiment (FIG. 10A). In addition, we never observed signs for autoimmunity or excessive inflammation at the site of injection upon vaccination with rBCG nor in the lung up to 200 days post MTB infection.

In a first attempt to compare data from experimental TB in mice with human data, we analyzed cytokine profiles of frozen PBMCs from a phase I clinical trial with rBCG and pBCG. In a limited number of samples we detected IL17 production after rBCG, but not pBCG, vaccination. Th17 cells have been detected in peripheral blood of MTB-infected humans (17). Recently, IL17-producing CD4 T cells have been reported in adolescents vaccinated with a TB vaccine candidate composed of modified vaccinia virus Ankara expressing Ag85A (33). Responses peaked between days 7 and 28 post vaccination and declined thereafter. This is in line with our data showing elevated IL17 production at day 29 post vaccination in the rBCG group (FIG. 12). Thus, it is tempting to propose IL17 as a correlate of protection in TB vaccine trials.

In summary, we show that vaccination with rBCG leads to preferential generation of Th17 cells, likely dependent on intracellular recognition of bacterial components by Nod-2. These Th17 cells in turn accelerate recruitment of antigen-specific T cells to the lung. Ultimately, this cascade of events results in earlier containment of MTB and hence, in superior protection by rBCG as compared to pBCG. We detect IL17 production exclusively by PBMC from rBCG-vaccinated volunteers in a successfully completed phase I clinical trial. Since IL17 seems instrumental for accelerated recruitment of antigen-specific T cells to the sites of MTB replication, future TB vaccines should be tailored to concomitantly induce balanced Th1 and Th17 responses.

REFERENCE LIST

1. Tuberculosis Fact Sheet N° 104 March. WHO. 2010;
2. Calmette A. Sur la vaccination préventive des enfants nouveau-nés contre tuberculose par le BCG. Ann Inst Pasteur. 1929; 41201-232.
3. Reece S T, Kaufmann S. H. Rational design of vaccines against tuberculosis directed by basic immunology. Int J Med Microbiol. 2008; 298(1-2):143-150.
4. Trunz B B, Fine P., Dye C. Effect of BCG vaccination on childhood tuberculous meningitis and miliary tuberculosis worldwide: a meta-analysis and assessment of cost-effectiveness. Lancet. 2006; 367(9517):1173-1180.
5. Colditz G A, Brewer T. F., Berkey C. S., Wilson M. E., Burdick E., Fineberg H. V. et el. Efficacy of BCG vaccine in the prevention of tuberculosis. Meta-analysis of the published literature. JAMA. 1994; 271(9):698-702.
6. Skeiky Y A, Sadoff J. C. Advances in tuberculosis vaccine strategies. Nat Rev Microbiol. 2006; 4(6):469-476.
7. Kaufmann S H, Baumann S., Nasser Eddine A. Exploiting immunology and molecular genetics for rational vaccine design against tuberculosis. Int J Tuberc Lung Dis. 2006; 10(10):1068-1079.
8. Fletcher H A. Correlates of immune protection from tuberculosis. Curr Mol Med. 2007; 7(3):319-325.
9. Goldsack L, Kirman J. R. Half-truths and selective memory: Interferon gamma, CD4(+) T cells and protective memory against tuberculosis. Tuberculosis (Edinb). 2007; 87(6):465-473.
10. Tchilian E Z, Desel C., Forbes E. K., Bandermann S., Sander C. R., Hill A. V. et el. Immunogenicity and protective efficacy of prime-boost regimens with recombinant (delta)ureC hly+ *Mycobacterium bovis* BCG and modified vaccinia virus ankara expressing *M. tuberculosis* antigen 85A against murine tuberculosis. Infect Immun. 2009; 77(2):622-631.
11. Pearl J E, Saunders B., Ehlers S., Orme I. M., Cooper A. M. Inflammation and lymphocyte activation during mycobacterial infection in the interferon-gamma-deficient mouse. Cell Immunol. 2001; 211(1):43-50.
12. Grode L, Seiler P., Baumann S., Hess J., Brinkmann V., Nasser Eddine A. et el. Increased vaccine efficacy against tuberculosis of recombinant *Mycobacterium bovis* bacille Calmette-Guerin mutants that secrete listeriolysin. J Clin Invest. 2005; 115(9):2472-2479.
13. Khader S A, Bell G. K., Pearl J. E., Fountain J. J., Rangel-Moreno J., Cilley G. E. et el. IL-23 and IL-17 in the establishment of protective pulmonary CD4+ T cell responses after vaccination and during *Mycobacterium tuberculosis* challenge. Nat Immunol. 2007; 8(4):369-377.
14. Darrah P A, Patel D. T., De Luca P. M., Lindsay R. W., Davey D. F., Flynn B. J. et el. Multifunctional TH1 cells define a correlate of vaccine-mediated protection against *Leishmania major*. Nat Med. 2007; 13(7):843-850.
15. Korn T, Bettelli E., Gao W., Awasthi A., Jager A., Strom T. B. et el. IL-21 initiates an alternative pathway to induce proinflammatory T(H)17 cells. Nature. 2007; 448(7152): 484-487.
16. Liang S C, Tan X. Y., Luxenberg D. P., Karim R., Dunussi-Joannopoulos K., Collins M. et el. Interleukin (IL)-22 and IL-17 are coexpressed by Th17 cells and cooperatively enhance expression of antimicrobial peptides. J Exp Med. 2006; 203(10):2271-2279.
17. Scriba T J, Kalsdorf B., Abrahams D. A., Isaacs F., Hofmeister J., Black G. et el. Distinct, Specific IL-17- and IL-22-Producing CD4+ T Cell Subsets Contribute to the Human Anti-Mycobacterial Immune Response. J Immunol. 2008; 180(3):1962-1970.
18. Lockhart E, Green A. M., Flynn J. L. IL-17 production is dominated by gammadelta T cells rather than CD4 T cells during *Mycobacterium tuberculosis* infection. J Immunol. 2006; 177(7):4662-4669.
19. van Beelen A J, Zelinkova Z., Taanman-Kueter E. W., Muller F. J., Hommes D. W., Zaat S. A. et el. Stimulation of the intracellular bacterial sensor NOD2 programs dendritic cells to promote interleukin-17 production in human memory T cells. Immunity. 2007; 27(4):660-669.
20. Ferwerda G, Girardin S. E., Kullberg B. J., Le Bourhis L., de Jong D. J., Langenberg D. M. et el. NOD2 and toll-like receptors are nonredundant recognition systems of *Mycobacterium tuberculosis*. PLoS Pathog. 2005; 1(3):279-285.
21. Flynn J L, Chan J., Triebold K. J., Dalton D. K., Stewart T. A., Bloom B. R. An essential role for interferon gamma in resistance to *Mycobacterium tuberculosis* infection. J Exp Med. 1993; 178(6):2249-2254.
22. Flynn J L, Goldstein M. M., Chan J., Triebold K. J., Pfeffer K., Lowenstein C. J. et el. Tumor necrosis factor-alpha is required in the protective immune response against *Mycobacterium tuberculosis* in mice. Immunity. 1995; 2(6):561-572.
23. Williams M A, Tyznik A. J., Bevan M. J. Interleukin-2 signals during priming are required for secondary expansion of CD8+ memory T cells. Nature. 2006; 441(7095):890-893.
24. Happel K I, Dubin P. J., Zheng M., Ghilardi N., Lockhart C., Quinton L. J. et el. Divergent roles of IL-23 and IL-12 in host defense against *Klebsiella pneumoniae*. J Exp Med. 2005; 202(6):761-769.
25. Khader S A, Pearl J. E., Sakamoto K., Gilmartin L., Bell G. K., Jelley-Gibbs D. M. et el. IL-23 compensates for the absence of IL-12p70 and is essential for the IL-17 response during tuberculosis but is dispensable for protection and antigen-specific IFN-gamma responses if IL-12p70 is available. J Immunol. 2005; 175(2):788-795.
26. Steinman L. A brief history of T(H)17, the first major revision in the T(H)1/T(H)2 hypothesis of T cell-mediated tissue damage. Nat Med. 2007; 13(2):139-145.
27. Singh S P, Zhang H. H., Foley J. F., Hedrick M. N., Farber J. M. Human T cells that are able to produce IL-17 express the chemokine receptor CCR6. J Immunol. 2008; 180(1):214-221.
28. Liu H, Rohowsky-Kochan C. Regulation of IL-17 in human CCR6+ effector memory T cells. J Immunol. 2008; 180(12):7948-7957.
29. Scapini P, Laudanna C., Pinardi C., Allavena P., Mantovani A., Sozzani S. et el. Neutrophils produce biologically active macrophage inflammatory protein-3alpha (MIP-3alpha)/CCL20 and MIP-3beta/CCL19. Eur J Immunol. 2001; 31(7):1981-1988.
30. Lee J S, Lee J. Y., Son J. W., Oh J. H., Shin D. M., Yuk J. M. et el. Expression and regulation of the CC-chemokine ligand 20 during human tuberculosis. Scand J Immunol. 2008; 67(1):77-85.
31. Forbes E K, Sander C., Ronan E. O., McShane H., Hill A. V., Beverley P. C. et el. Multifunctional, high-level cytokine-producing Th1 cells in the lung, but not spleen, correlate with protection against *Mycobacterium tuberculosis* aerosol challenge in mice. J Immunol. 2008; 181(7):4955-4964.
32. Abel B, Tameris M., Mansoor N., Gelderbloem S., Hughes J., Abrahams D. et el. The novel tuberculosis vaccine, AERAS-402, induces robust and polyfunctional CD4+ and CD8+ T cells in adults. Am J Respir Crit Care Med. 2010; 181(12):1407-1417.
33. Scriba T J, Tameris M., Mansoor N., Smit E., van der Merwe L., Isaacs F. et el. Modified vaccinia Ankara-expressing Ag85A, a novel tuberculosis vaccine, is safe in adolescents and children, and induces polyfunctional CD4+ T cells. Eur J Immunol. 2010; 40(1):279-290.
34. Roark C L, Simonian P. L., Fontenot A. P., Born W. K., O'Brien R. L. gammadelta T cells: an important source of IL-17. Curr Opin Immunol. 2008; 20(3):353-357.
35. Rachitskaya A V, Hansen A. M., Horai R., Li Z., Villasmil R., Luger D. et el. Cutting edge: NKT cells constitutively express IL-23 receptor and RORgammat and rapidly produce IL-17 upon receptor ligation in an IL-6-independent fashion. J Immunol. 2008; 180(8):5167-5171.
36. Torchinsky M B, Garaude J., Martin A. P., Blander J. M. Innate immune recognition of infected apoptotic cells directs T(H)17 cell differentiation. Nature. 2009; 458(7234):78-82.
37. Meng G, Zhang F., Fuss I., Kitani A., Strober W. A mutation in the Nlrp3 gene causing inflammasome hyperactivation potentiates Th17 cell-dominant immune responses. Immunity. 2009; 30(6):860-874.
38. Mariathasan S, Weiss D. S., Newton K., McBride J., O'Rourke K., Roose-Girma M. et el. Cryopyrin activates the inflammasome in response to toxins and ATP. Nature. 2006; 440(7081):228-232.
39. Nakae S, Nambu A., Sudo K., Iwakura Y. Suppression of immune induction of collagen-induced arthritis in IL-17-deficient mice. J Immunol. 2003; 171(11):6173-6177.
40. Langrish C L, Chen Y., Blumenschein W. M., Mattson J., Basham B., Sedgwick J. D. et el. IL-23 drives a pathogenic T cell population that induces autoimmune inflammation. J Exp Med. 2005; 201(2):233-240.
41. Hellings P W, Kasran A., Liu Z., Vandekerckhove P., Wuyts A., Overbergh L. et el. Interleukin-17 orchestrates the granulocyte influx into airways after allergen inhalation in a mouse model of allergic asthma. Am J Respir Cell Mol Biol. 2003; 28(1):42-50.
42. Kursar M, Koch M., Mittrucker H. W., Nouailles G., Bonhagen K., Kamradt T. et el. Cutting Edge: Regulatory T cells prevent efficient clearance of *Mycobacterium tuberculosis*. J Immunol. 2007; 178(5):2661-2665.
43. Brosch R, Gordon S V, Garnier T, Eiglmeier K, Frigui W, Valenti P, Dos Santos S, Duthoy S, Lacroix C, Garcia-Pelayo C, Inwald J K, Golby P, Garcia J N, Hewinson R G, Behr M A, Quail M A, Churcher C, Barrell B G, Parkhill J, Cole S T, Proc Natl Acad Sci USA. 2007 Mar. 27; 104 (13): 5596-601. Epub 2007 Mar. 19.

The invention claimed is:

1. A method for determining the efficacy of a mycobacterial vaccine, comprising administering a vaccine comprising a recombinant *Mycobacterium* which comprises a recombinant nucleic acid molecule encoding a fusion polypeptide comprising (a) a domain capable of eliciting an immune Response and (b) a phagolysosomal escape domain, to a subject and determining the Th17 immune response to purified protein derivative antigens in said mycobacterial vaccinated subject, wherein a detectable Th17 immune response is indicative for protective immunity against mycobacteria in said subject.

2. The method of claim 1, wherein the vaccine is a live vaccine.

3. The method of claim 1, wherein the *Mycobacterium* is urease-deficient.

4. The method of claim 3, wherein the *Mycobacterium* is rBCGΔUreC::Hly$^+$::Hyg$^+$.

5. The method of claim 1, wherein the vaccine is a subunit vaccine.

6. The method of claim 1, wherein determining the Th17 immune response to purified protein derivative antigens comprises subjecting a sample comprising immune cells from said vaccinated subject to a restimulation with an immunogen corresponding to the purified protein derivative antigen immunogen in said vaccine and determining the presence and/or amount of Th17 immune response associated cells in said sample.

7. The method of claim 1, wherein determining the Th17 immune response comprises determining IL7.

8. The method of claim 1, wherein the subject is a mammal.

9. The method of claim 1, wherein the Th17 immune response is determined 20-50 days after vaccination.

10. A reagent kit for determining the efficacy of a mycobacterial vaccine, comprising (a) a reagent for restimulating immune cells previously stimulated by a mycobacterial vaccine comprising a recombinant nucleic acid molecule encoding a fusion polypeptide comprising (a) a domain capable of eliciting an immune response and (b) a phagolysosomal escape domain, and (b) a reagent for detecting a Th17 immune response to purified protein derivative antigens.

11. The method of claim 7, wherein the mammal is a human.

12. The method of claim 1, wherein the vaccine is a rBCG or pBCG vaccine.

13. The method of claim 1, wherein the vaccine is a vaccine against pulmonary mycobacterial infections.

14. The method of claim 13, wherein the vaccine is a vaccine against tuberculosis.

15. The method of claim 6, wherein IL17 is determined using immunological methods.

* * * * *